United States Patent [19]

Ueno et al.

[11] Patent Number: 5,229,529
[45] Date of Patent: Jul. 20, 1993

[54] METHOD OF PRODUCING α,β-UNSATURATED KETOLACTONES

[75] Inventors: Ryuji Ueno, Nishinomiya; Tomio Oda, Sanda, both of Japan

[73] Assignee: R-Tech Ueno Ltd., Osaka, Japan

[21] Appl. No.: 861,518

[22] Filed: Apr. 1, 1992

[30] Foreign Application Priority Data

Apr. 4, 1991 [JP] Japan .................................. 3-71483

[51] Int. Cl.$^5$ ........................................ C07D 307/935
[52] U.S. Cl. .................................................. 549/305
[58] Field of Search ........................................ 549/305

[56] References Cited

U.S. PATENT DOCUMENTS

| | | | |
|---|---|---|---|
| 4,032,576 | 6/1977 | Nelson | 568/380 |
| 4,788,299 | 11/1988 | Riefling | 549/305 |
| 4,810,805 | 3/1989 | Shibasaki et al. | 549/305 |

FOREIGN PATENT DOCUMENTS

| | | |
|---|---|---|
| 0219580 | 4/1987 | European Pat. Off. . |
| 2655004 | 6/1978 | Fed. Rep. of Germany . |
| 8901936 | 3/1989 | World Int. Prop. O. . |

*Primary Examiner*—C. Warren Ivy
*Assistant Examiner*—A. A. Owens
*Attorney, Agent, or Firm*—Sughrue, Mion, Zinn, Macpeak & Seas

[57] ABSTRACT

The present invention provides a method of preparing α,β-unsaturated ketolactones which are useful for production of prostaglandins having one or more halogen substituent(s) at the 16 or 17 portion in high yield, in which, a dimethyl (2-oxoalkyl) phosphonate having one or more halogen substituents, a starting material, is reacted with a bicyclolactone aldehyde under the presence of an alkali metal hydride and a zinc compound.

5 Claims, No Drawings

METHOD OF PRODUCING α,β-UNSATURATED KETOLACTONES

BACKGROUND OF THE INVENTION

1. Field of the Invention

The present invention relates to a method for producing α,β-unsaturated ketolactones which are useful as synthetic intermediates for prostaglandins.

2. Description of the Prior Art

During the study of various kinds of prostaglandin derivatives, it has been found that there exist many prostaglandins having the prostanoic acid skeletone in which has at least one halogen atom, especially fluorine atom, at the 16- or 17- position [16(17)-mono or 16,16 (17,17)-dihalo-prostaglandins] represented by the following formula:

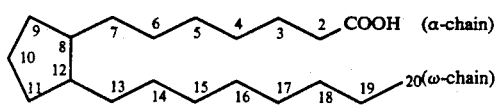

that exhibit characteristic pharmacological activities.

Corey method has been well known for a long time and is still a typical synthetic procedure of prostaglandins.

· The Corey method includes the step of producing an α,β-unsaturated ketolactone (III) from Corey lactone via Corey aldehyde (II):

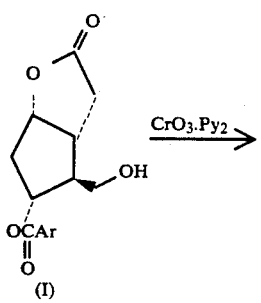

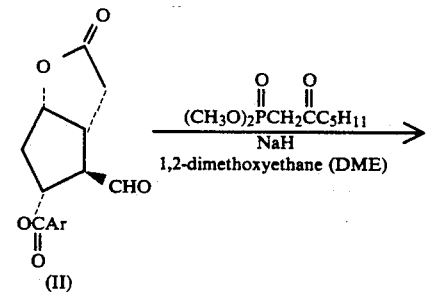

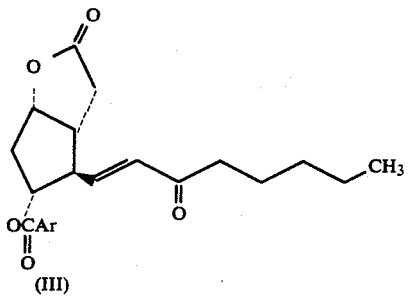

[wherein Ar represents an aromatic group.]

Corey lactone (I) is oxidized to Corey aldehyde (II) using the complex of pyridine and chromium trioxide (so called Collins oxidation), followed by a reaction between this aldehyde and an anion generated by reacting a dimethyl (2-oxoalkyl)phosphonate with sodium hydride to give the α,β-unsaturated ketolactone (III).

These reactions are simply considered to be applicable to the synthesis of 16(17)-mono or 16,16(17,17)-dihalo-prostaglandins. However, when dimethyl (2-oxoalkyl) phosphonates having a or two halogen atoms at the 3-position are used as a replacement of the said phosphonate, the yield of the desired α,β-unsaturated ketolactone decreases to a level of below 10%.

Many attempts have been made that reactions are carried out under the presence of sodium hydride and a copper compound, or a thallium compound, to improve the yield. Use of the copper compound, however, does not result in an adequate improvement in the yield, while the thallium compound, showing improvement in the yield to some extent as it does, is toxic property and is very expensive. Thus, there has been a desire for further improvement in the reaction step.

SUMMARY OF THE INVENTION

The object of the present invention is to provide a method of producing an α,β-unsaturated ketolactone (III) substituted with one or two halogen atoms at the position which corresponds to the 16 or 17 position of the prostaglandin skeleton when they are derived from the α,β-unsaturated ketolactones.

As aforementioned the yield of the α,β-unsaturated ketolactone is low, when it is produced by the reaction of Corey aldehyde with a dimethyl (2-oxoalkyl) phosphonate substituted with one or two halogen atoms at the 3-position using sodium hydride and a copper compound.

According to the present invention the yield of the α,β-unsaturated ketolactones is improved using a zinc compound instead of a copper compound.

Thus there is provided a method of producing α,β-unsaturated ketolactones represented by formula (3):

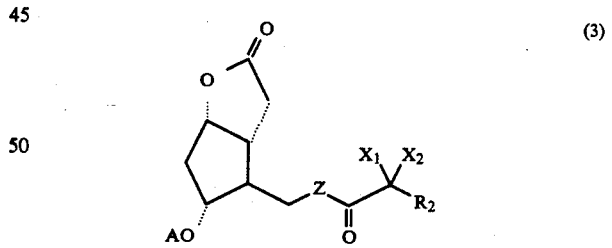

wherein A represents a hydroxyl protection group; $X_1$ and $X_2$ represent a hydrogen atom or a halogen atom respectively, providing at least one of $X_1$ and $X_2$ is a halogen atom;

$R_2$ represents an alkyl group having 1 to 10 carbon atoms which may have a branch, a double bond, an alkoxy group, a phenyl group or a phenoxy group or

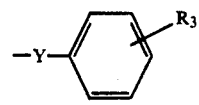

wherein Y represents a single bond or an oxygen atom; and $R_3$ represents a hydrogen or halogen atom, or an alkyl or a halogenated alkyl group and Z represents =CH— or —CH=CH—;

which comprises reacting a compound represented by formula (1):

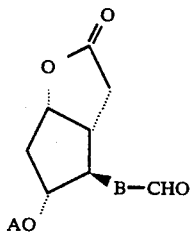

wherein A has the same meaning as described above and B represents a single bond or —CH$_2$—;

with a compound represented by formula:

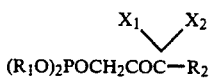

wherein $X_1$, $X_2$ and $R_2$ have the same meanings as described above and $R_1$ represents an alkyl group having 1 to 4 carbon atoms; under the presence of an alkali metal hydride and a zinc compound.

DETAILED DESCRIPTION OF THE INVENTION

The present invention relates to a method of producing $\alpha,\beta$-unsaturated ketolactones, which comprises reacting a bicyclolactone aldehyde with a dimethyl (2-oxoalkyl) phosphonate which is substituted by at least one halogen atom at the 3-position of the said alkyl group, under the presence of an alkali metal hydride and a zinc compound.

The bicyclolactone aldehyde (1) which is a starting material of the present invention is represented by the following formula (1):

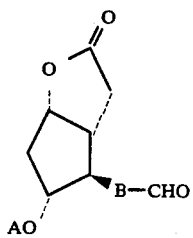

[wherein A represents a hydroxyl protection group for hydroxyl groups, for instance:

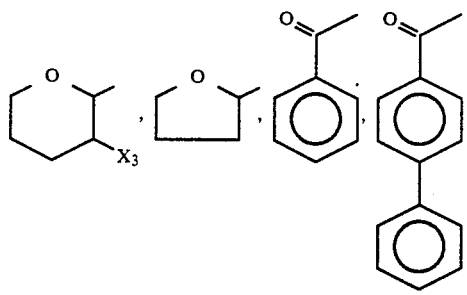

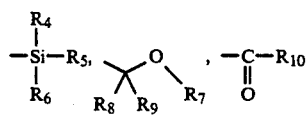

(wherein $X_3$ is a hydrogen or halogen atom, $R_4$, $R_5$ and $R_6$ are an alkyl group having $C_1$-$C_4$ carbon atoms or a phenyl group, $R_7$ is an alkyl group with $C_1$-$C_4$ carbon atoms, which may have an alkoxy or a sillyl group, and $R_{10}$ is an alkyl group with $C_1$-$C_4$ carbon atoms) and wherein B represents a simple bond or a methylene group, —CH$_2$—]. This bicyclolactone aldehyde (1) can be obtained from Corey lactone (I) through an oxidation reaction using dimethylsulfoxide (hereinafter simply referred to as DMSO oxidation). Examples of this DMSO oxidation are so-called Pfilzner-Moffatt oxidation in which DMSO, dicyclohexylcarbodiimide, trifluoroacetic acid and pyridine are used, so-called Swern oxidation in which DMSO, oxarylchloride and triethylamine are used and so-called Parikh-Doering oxidaion in which DMSO, a complex of sulfur trioxide and triethylamine. DMSO oxidation allows the reaction to be easily controlled and the alcohols to be oxidized to the corresponding aldehydes in high yields since the aldehydes produced are prevented from the further oxidation to the corresponding carboxylic acid.

This bicyclolactone aldehyde (1) can also be prepared by the oxidation, a similar reaction as described above, of bicyclolactone carring an alkyl sidechain elongated by one in the number of the carbon atoms by subjecting Corey lactone (I) to the reactions as shown below.

For the carbon-number increasing reaction, a leaving group (tosyl group, for example) is first introduced into Corey lactone (I) having an appropriate protection group (4-phenylbenzoyl group, for example) for the 7-hydroxylgroup followed by reacting a cyanide generating compound to yield a nitrile compound. The hydroxyl protection group is eliminated from this nitrile compound and the cyanogroup is then hydrolysed to the carboxyl group. Then, after introducing another protection group (acetyl group, for example) for the 7-hydroxyl group, the carboxyl group is reduced to yield the bicyclolactone carring an alkyl sidechain elongated by one in the number of carbon atoms.

A feature of the present invention exists in that the condensation reaction between bicyclolactone aldehyde (1) and a dimethyl (2-oxoalkyl) phosphonate to yield an $\alpha,\beta$-unsaturated ketolactone (3) is carried out under the presence of an alkali metal hydride and a zinc compound.

In regard to alkali metal hydrides, hydrides of alkali metals or alkali earth metals can be used, and their examples include sodium hydride, potassium hydride or calcium hydride, and sodium hydride is particularly preferable.

Zinc halides such as zinc chloride, zinc bromide, or zinc salts of organic acid such as zinc acetate may be used for the zinc compounds, and zinc halides are particularly preferable.

The amount of the alkali metal hydride to be used is preferably about 1 molar equivalent relative to the amount of a dimethyl (2-oxoalkyl) phosphonate (2) and the amount of the zinc compound is preferably from 0.5 to 1 molar equivalent relative to the amount of a dimethyl (2-oxoalkyl) phosphonate (2).

Reaction solvents are not particularly specified, but the solvents such as tetrahydrofurane, dimethoxyethane, dichloromethane, ethylether, 1,4-dioxane, benzene and toluene are preferable.

The amount of the reaction solvent is preferable in the range of 5 to 30 ml relative to 1 g of Corey aldehyde (1), and the range of 10 to 20 ml is particularly preferable.

The reaction temperature range may be from 0° to 50° C. and the range of 10° to 50° C. is particularly preferable.

The reaction time may be in the range of 4 to 72 hours, preferably in the range of 24 to 50 hours.

The present invention is illustrated by the following examples. But it should be construed that the present invention is not limited to these examples.

EXAMPLE 1

Oxallyl chloride (2M in $CH_2Cl_2$ 176.7 ml) was added to dichloromethane (530 ml) and, after cooling to −78° C., a solution of dimethylsulfoxide (50.7 ml; hereinafter, referred to as DMSO) in dichloromethane (50.7 ml) was added dropwise over a period of 20 minutes with stirring at −78° C. Into the above solution obtained was added dropwise solution of Corey lactone (A) (45.3 g)

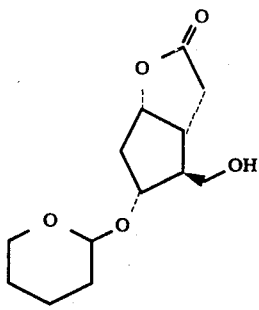

(A)

in dichloromethane (200 ml), and after stirring at −50° C. for 1 hour, triethylamine (101.3 ml) was added dropwise, followed by stirring for 1 hour at the temperature increased to −20° C. This solution was poured into a saturated aqueous solution of ammonium chloride. After a usual work-up, the aldehyde (B)

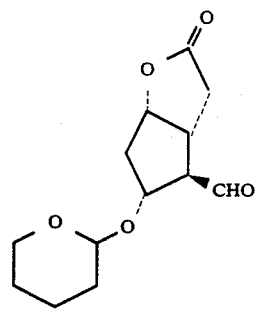

(B)

was obtained.

Sodium hydride (60%, 8.48 g) was suspended in THF (300 ml) at 0° C., into which a solution of dimethyl (3,3-difluoro-2-oxoheptyl)phosphonate (54.8 g) in THF (100 ml) was added, and the mixture was stirred for 20 minutes. To the resultant was added zinc chloride (14.5 g) with stirring for 2 hours at room temperature. The mixture was cooled to 0° C., followed by addition of a solution of the above-described aldehyde in THF (200 ml), and by stirring for 18 hours at room temperature. The additional anion prepared from dimethyl (3,3-difluoro-2-oxoheptyl) phosphonate (22.8 g), sodium hydride (60%, 3.5 g) and zinc chloride (6.0 g) was added, and the mixture was stirred for 6 hours at room temperature, followed by addition of acetic acid (12.1 ml) at 0° C. The crude product obtained after the usual work-up was purified on a silica gel column and (1S, 5R, 6R, 7R)-6-[(E)-4,4-difluoro-3-oxo-1-octenyl]-7-tetrahydropyranyloxy-2-oxabicyclo[3. 3. 0]octan-3-one (referred to as α,β-unsaturated ketolactone (C) hereinafter) was obtained.

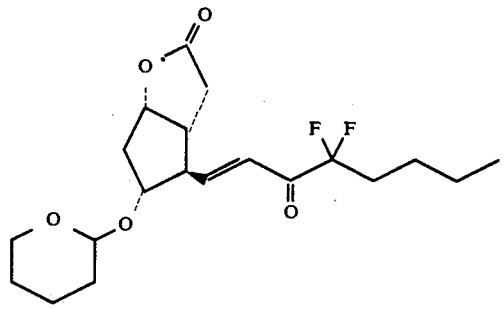

(C)

Yield: 52.8 g (77%)

COMPARATIVE EXAMPLE 1

An aldehyde (B) was obtained by subjecting Corey lactone (A) (2.37 g) to Swern oxidation using oxalyl chloride (1.8 ml), DMSO (2.9 ml) and triethylamine (12.5 ml) in dichloromethane.

Dimethyl (3,3-difluoro-2-oxoheptyl)phosphonate was added dropwise to a solution of thallium ethoxide (0.06 ml) in methylene chloride (60 ml), and the solution was stirred for 30 minutes. The reaction temperature was adjusted to 0° C. and a solution of the aldehyde (B) in dichloromethane (30 ml) was added dropwise, followed by stirring for 5 hours at room temperature. The crude product obtained after the usual work-up was chromatographed on a column of silica gel to yield the α,β-unsaturated ketolactone (C).

Yield: 2.35 g (66%)

COMPARATIVE EXAMPLE 2

Aldehyde (B) was obtained by subjecting Corey lactone (A) (1.25 g) to Swern oxidation using oxalyl chloride (0.88 ml), DMSO (1.42 ml) and triethylamine (6.1 ml) in dichloromethane.

Sodium hydride (60%, 0.195 g) was suspended in 30 ml of THF, and a solution of dimethyl (3,3-difluoro-2-oxoheptyl)phosphonate (1.27 g) in THF (5 ml) was added dropwise to the suspension, followed by stirring for 1 hour. Copper iodide (0.929 g) was added to the solution and the mixture was stirred for 1 hour at room temperature. After adjusting the reaction temperature to 0° C., an aldehyde (B) solution in THF (10 ml) was added dropwise, followed by stirring overnight at room temperature. The crude product obtained after the usual work-up was chromatographed on a column of silica gel, thereby obtaining the α,β-unsaturated ketolactone (C).

Yield: 0.431 g (23%)

COMPARATIVE EXAMPLE 3

Aldehyde (B) was obtained by subjecting Corey lactone (A) (0.523 g) to Swern oxidation by the same method as described in Comparative Example 2.

Sodium hydride (60%, 0.082 g) was suspended in THF and a THF solution of dimethyl (3,3-difluoro-2-oxoheptyl) phosphonate (0.464 g) was added to the suspension, and the mixture was stirred for 30 minutes. The reaction temperature was adjusted to 0° C. and the THF solution of aldehyde (B) obtained as described above was added and the mixture was stirred overnight. The residue obtained after the usual work-up was chomatographed on a column of silica gel, but no α,β-unsaturated ketolactone (C) was obtained.

EXAMPLE 2

Dimethyl(3,3-difluoro-2-oxononyl)phosphonate (3.918 g) and sodium hydride (60%, 0.547 g) was stirred in THF (30 ml) for 15 minutes at room temparature. Zinc chloride (0.933 g) was added, and the solution was stirred for 2 hours. To the solution was added Corey aldehyde (1.69 g) in THF (20 ml), which was prepared from Corey lactone according to the same method as described in Example 1, and the solution was stirred for 50 hours at room temperature. The crude product obtained by the usual work-up was chromatographed to give (1S, 5R, 6R, 7R)-6-[(E)-4,4-difluoro-3-oxo-1-decenyl]-7-tetrahydropyranyloxy-2-oxabicyclo[3. 3. 0]octan-3-one was obtained.

Yield: 1.789 g (65%)

What is claimed is:

1. A method of producing α,β-unsaturated ketolactones, which comprises reacting a bicyclolactone aldehyde with a dimethyl (2-oxoalkyl) phosphonate which is substituted by at least one halogen atom at the 3-position of the said alkyl group, under the presence of an alkali metal hydride and a zinc compound.

2. A method according to claim 1, wherein the bicyclolactone aldehyde is represented by the formula:

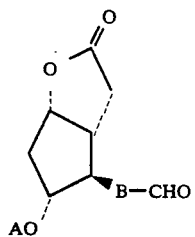

wherein A represents a hydroxyl protection group and B represents a single bond or —$CH_2$— and a dimethyl (2-oxoalkyl) phosphonate is represented by the formula:

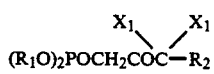

wherein $X_1$ and $X_2$ represent a hydrogen atom or a halogen atom respectively, providing at least one of $X_1$ and $X_2$ is a halogen atom; $R_1$ represents an alkyl group having 1 to 4 carbon atoms; $R_2$ represents an alkyl group having 1 to 10 carbon atoms which may have a branch, a double bond, an alkoxy group, a phenyl group or a phenoxy group or

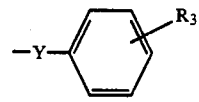

wherein Y represents a single bond or an oxygen atom; and $R_3$ represents a hydrogen or halogen atom, or an alkyl or a halogenated alkyl group.

3. A method according to claim 2, wherein at least one of $X_1$ and $X_2$ is a fluorine atom.

4. A method according to claim 1, wherein the α,β-unsaturated ketolactones are represented by the formula:

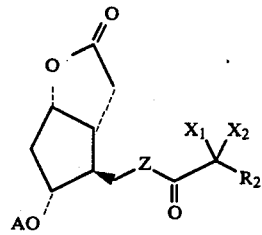

wherein A, $X_1$, $X_2$ and $R_2$ have the same meanings as described above and Z represents =CH— or —CH=CH—.

5. A method of producing a α,β-unsaturated ketolactones represented by formula (3):

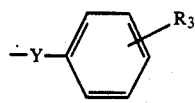

(3)

wherein A represents a hydroxyl protection group; $X_1$ and $X_2$ represent a hydrogen atom or a halogen atom respectively, providing at least one of $X_1$ and $X_2$ is a halogen atom;

$R_2$ represents an alkyl group having 1 to 10 carbon atoms which may have a branch, a double bond, an alkoxy group, a phenyl group or a phenoxy group or

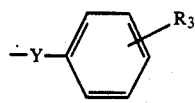

wherein Y represents a single bond or an oxygen atom; and $R_3$ represents a hydrogen or halogen atom, or an alkyl or a halogenated alkyl group and Z represents $=CH-$ or $-CH=CH-$;

which comprises reacting a compound represented by formula (1):

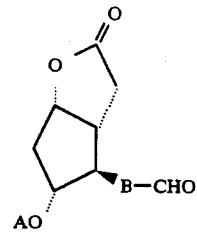

(1)

wherein A has the same meaning as described above and B represents a single bond or $-CH_2-$;
with a compound represented by formula:

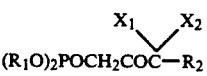

(2)

$(R_1O)_2POCH_2COC-R_2$ wherein $X_1$, $X_2$ and $R_2$ have the same meanings as described above and $R_1$ represents an alkyl group having 1 to 4 carbon atoms;

under the presence of an alkali metal hydride and a zinc compound.

* * * * *